United States Patent
Matsuura et al.

(10) Patent No.: US 10,012,572 B2
(45) Date of Patent: Jul. 3, 2018

(54) MASS-ANALYSIS DATA PROCESSING METHOD AND SYSTEM

(75) Inventors: Masaaki Matsuura, Koto-ku (JP); Masaru Ushijima, Koto-ku (JP); Masatoshi Wakui, Shinjuku-ku (JP); Mitsutoshi Setou, Hamamatsu (JP); Shigeki Kajihara, Uji (JP); Kiyoshi Ogawa, Kizugawa (JP)

(73) Assignee: Japanese Foundation for Cancer Research, Keio University, National University Corporation Hamamatsu, and Shimadzu Co. (JP)

( * ) Notice: Subject to any disclaimer, the term of this patent is extended or adjusted under 35 U.S.C. 154(b) by 1796 days.

(21) Appl. No.: 13/458,850

(22) Filed: Apr. 27, 2012

(65) Prior Publication Data

US 2012/0278037 A1  Nov. 1, 2012

(30) Foreign Application Priority Data

Apr. 28, 2011  (JP) ................. 2011-100492

(51) Int. Cl.
  *G01N 1/28* (2006.01)
  *G06F 15/00* (2006.01)
  *H01J 49/00* (2006.01)

(52) U.S. Cl.
  CPC ............ *G01N 1/28* (2013.01); *G06F 15/00* (2013.01); *H01J 49/0004* (2013.01); *H01J 49/0027* (2013.01)

(58) Field of Classification Search
  CPC .................. G01N 30/72; G01N 1/28
  See application file for complete search history.

(56) References Cited

U.S. PATENT DOCUMENTS

2007/0045527 A1* 3/2007 Ogawa ............... H01J 49/0004
                                                250/281
2007/0114388 A1* 5/2007 Ogawa ............... H01J 49/0004
                                                250/288
2009/0289184 A1* 11/2009 Deininger et al. ........... 250/282

FOREIGN PATENT DOCUMENTS

JP        2009-025268 A       2/2009

OTHER PUBLICATIONS

Translation of JP 2009025268 A.*
(Continued)

*Primary Examiner* — Alexander Satanovsky
*Assistant Examiner* — Lina Cordero
(74) *Attorney, Agent, or Firm* — Chris Mizumoto

(57) ABSTRACT

Provided is a technique for using an optical microscope image of an area on a sample to collect area-specific information characterizing each kind of biological tissue from imaging mass analysis data. On an optical image of a two-dimensional target area on a sample, a difference is examined in the kind of tissue or other features and areas are specified, each regarded as the same kind of tissue. When data processing is initiated, peak information is extracted, for each specified area, from mass spectrum data of all the measurement points. A peak method is applied to each area to extract peak information. Then, when a command to compare a set of areas is given, the peak information of those areas is collected. By comparing the peak information of different areas by a machine learning algorithm or similar judging technique, area-specific peak information is obtained, and this information is stored in memory.

8 Claims, 7 Drawing Sheets

(56) References Cited

OTHER PUBLICATIONS

Kiyoshi Ogawa et al., "Research and Development of Mass Microscope", Shimadzu Review, Mar. 31, 2006, vol. 62, Nos. 3-4, pp. 125-135.
Takahiro Harada et al., "Biological Tissue Analysis Using Mass Microscope", Shimadzu Review, Apr. 24, 2008, vol. 64, Nos. 3-4, pp. 139-146.
First Notification of Reason for Rejection issued in a corresponding Japanese Patent Application No. 2016-074892, dated Jan. 10, 2017.

* cited by examiner

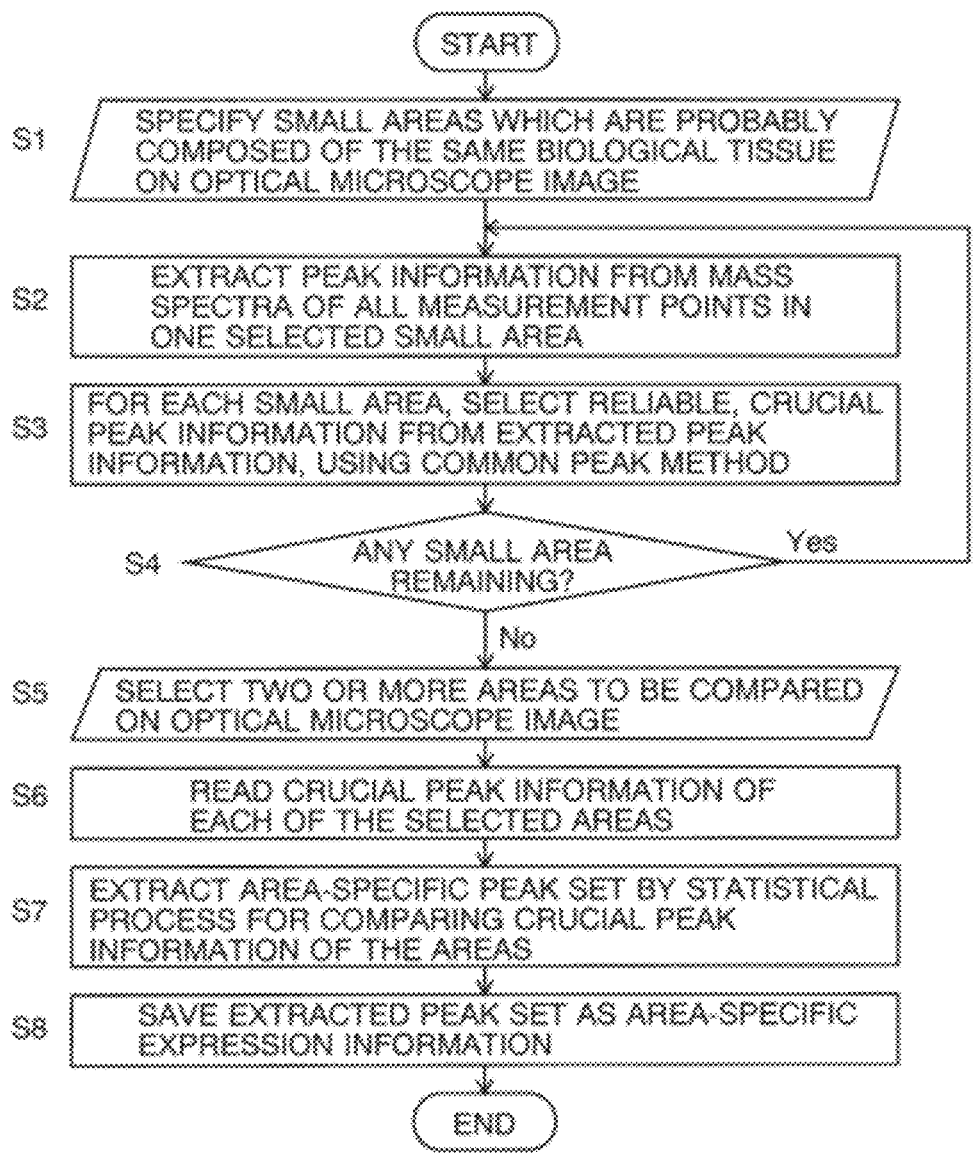

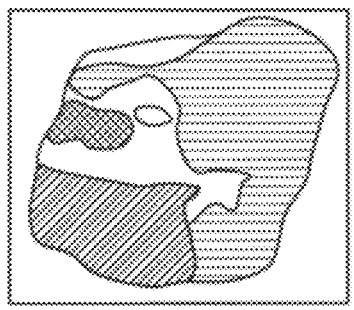
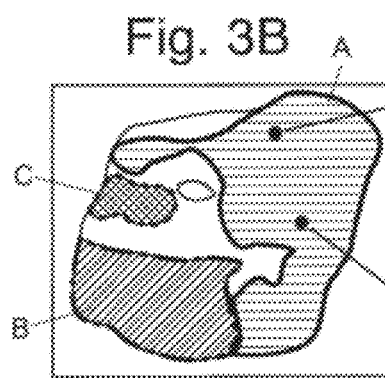
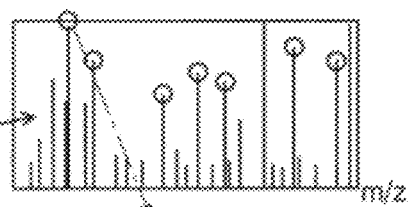
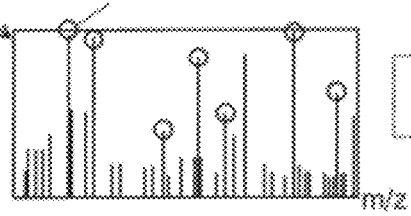
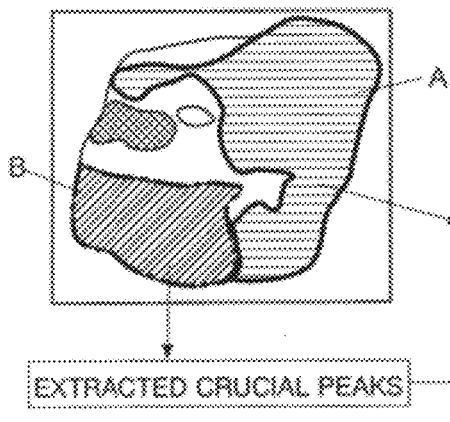

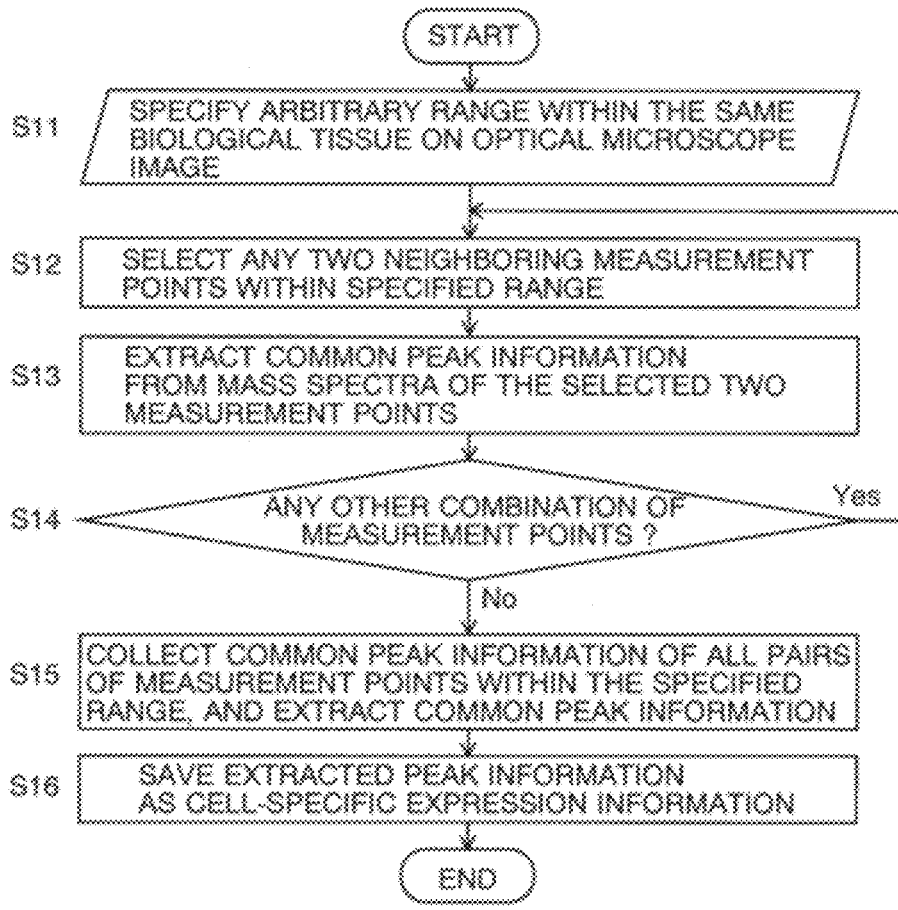
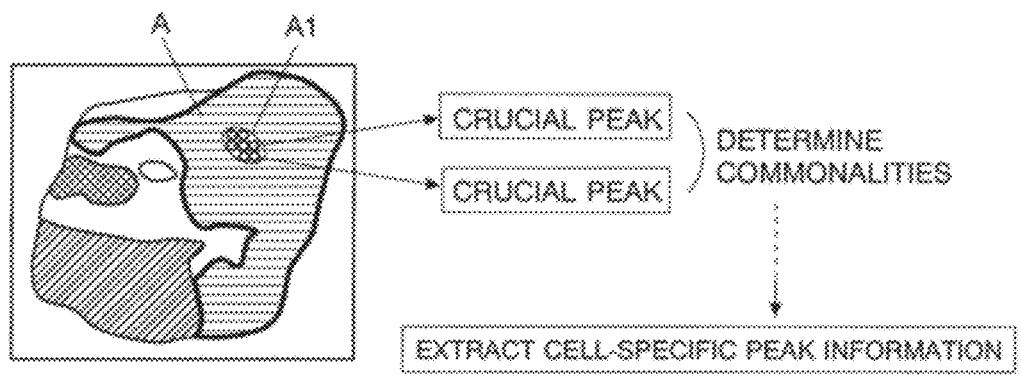

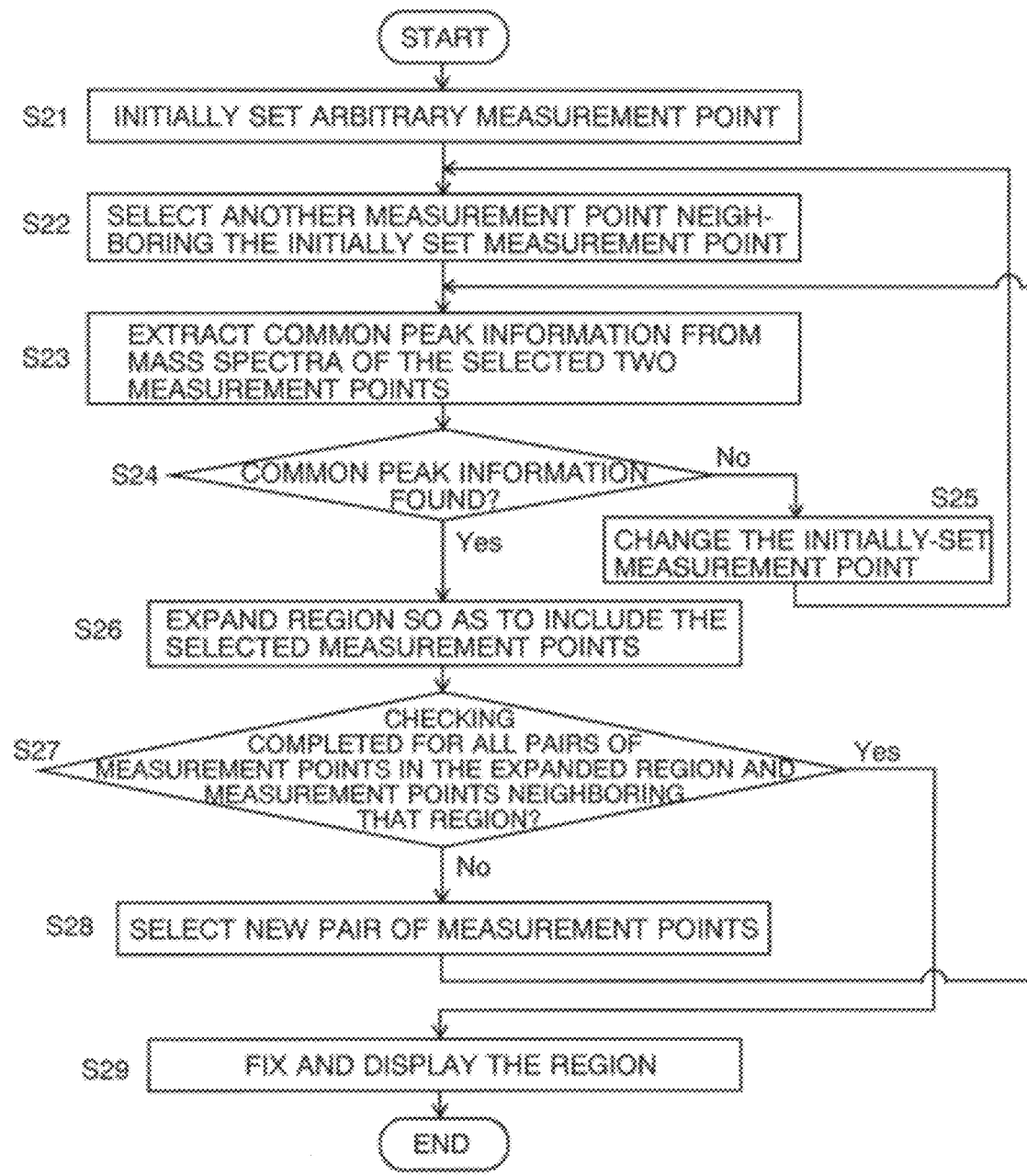

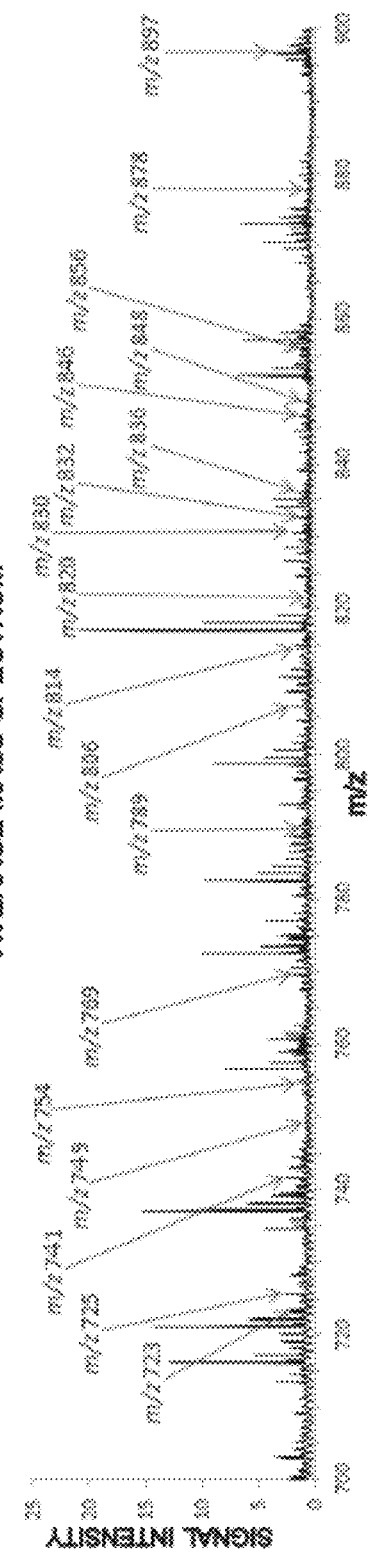
Fig. 9A AVERAGE MASS SPECTRUM
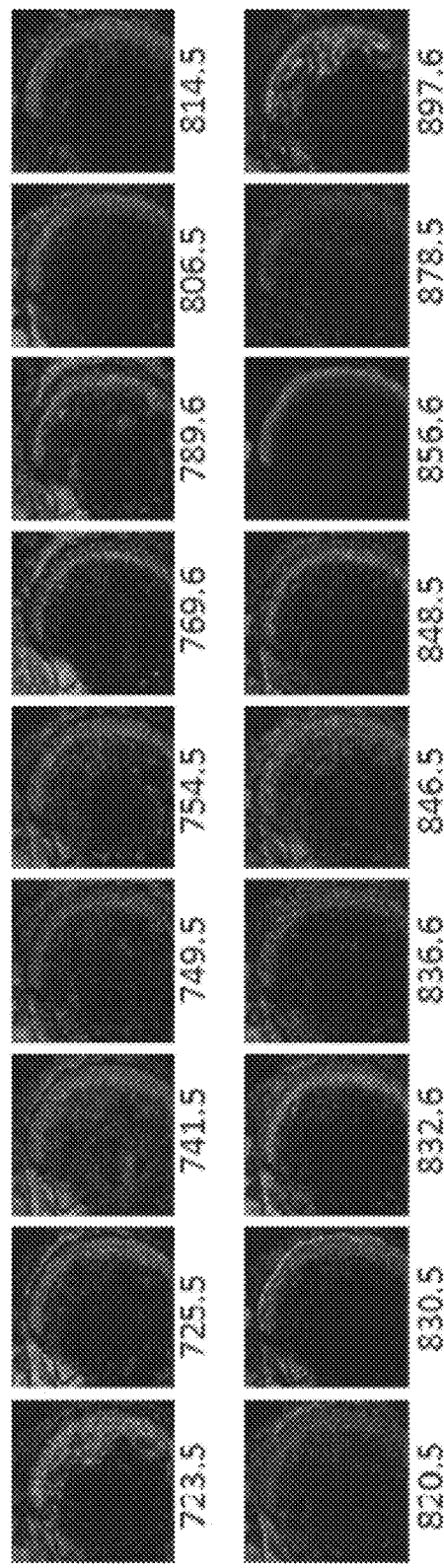
Fig. 9B SPATIAL DISTRIBUTIONS OF SUBSTANCES DETECTABLE BY METHOD ACCORDING TO PRESENT INVENTION BUT NOT BY CONVENTIONAL METHODS

MASS-ANALYSIS DATA PROCESSING METHOD AND SYSTEM

TECHNICAL FIELD

The present invention relates to a method and system for processing mass-analysis data collected by performing a mass analysis on each of a plurality of micro areas within a two-dimensional area on a sample.

BACKGROUND ART

In order to observe the morphology of a sample, such as a section of biological tissue, and simultaneously measure the distribution of the molecules existing in a predetermined area on the sample, a type of system called a mass microscope or an imaging mass spectrometer has been developed (for example, refer to Non-Patent Documents 1 and 2). These systems are capable of acquiring a distribution image (or mapping image) of the ions having a specific mass-to-charge ratio (m/z) included in any area specified on the sample based on a microscopic observation, while almost completely maintaining the original morphology of the sample without grinding or crushing the sample. Such systems are expected to be used, for example, to obtain distribution information of the proteins included in a living cell. Particularly, in the fields of medical care and pharmaceutical chemistry, those systems are expected to be used for determining a substance that specifically appears in a special type of cell, such as a cancer cell, to comprehend the distribution of the lesion.

Imaging mass spectrometers are capable of producing an optical microscope image on a sample and a mass-analysis result image at an arbitrary mass-to-charge ratio. The spatial resolution of the mass-analysis result image is normally much lower than that of the optical microscope image. For example, according to Patent Document 1, the spatial resolution of the optical microscope image is 0.5 µm, whereas that of the mass-analysis result image is as low as approximately 30 µm. Due to such a difference in the resolving power, for example, it often occurs that a plurality of kinds of tissue which have different colors or patterns and therefore can be clearly distinguished from each other on the optical microscope image cannot be distinguished on the mass-analysis result image. Accordingly, the optical microscope image can provide useful information for evaluating information obtained from the mass-analysis result image, such as the result of a statistical analysis of the mass-analysis result image, and for making judgment on that result.

An analyzing technique using the combination of the result of an imaging mass-analysis and an optical microscope image has been conventionally known from Patent Document 1. In the method disclosed in this document, after a mass spectrum is obtained for a specific micro area on a sample (e.g. a section of biological tissue), the difference between the obtained mass spectrum and a reference mass spectrum stored in a database is calculated to create a differential spectrum, and this differential spectrum is shown on a display screen. On the displayed differential spectrum, the peak of a substance that exists only in the aforementioned specific micro area (i.e. the peak not found in the reference mass spectrum) is shown by a solid line, and conversely, the peak of a substance that does not exist in the specific micro area but in the reference mass spectrum is shown by a dotted line. By performing a statistical analysis on the information of this differential spectrum, the micro area from which this spectrum has originated is classified into one of the classes (one group that can be regarded as the same kind of tissue). This classifying process is similarly performed for each micro area on the sample. As a result, the areas on the sample are classified according to their classes. However, as already noted, the size of each micro area for which the mass-analysis imaging is performed is not always sufficiently small. To address this problem, the analysis operator refers to a high-resolution optical microscope image to check the result of the classification of the micro areas by the aforementioned process, whereby the evaluation can be made with high reliability.

In the previously described conventional technique, although the result of the imaging mass analysis and the information presented by the optical microscope image are combined, this combination is actually nothing more than to simply compare the two kinds of images to evaluate the reliability of the result obtained by the imaging mass analysis. This is far from fully utilizing the two kinds of information. It is expected that a more active utilization of the optical microscope image, or more specifically, the use of an optical microscope image for the extraction or selection of the result of a mass-analysis imaging, will provide more useful and valuable information for analysis operators. However, no such technique has yet been proposed.

On the other hand, if different kinds of tissue cannot be distinguished by color, pattern or other visual information on the optical microscope image, i.e. if such visual information cannot be clearly recognized on the optical microscope image, the previously described conventional technique cannot provide useful information for the interpretation or evaluation of the result of the mass-analysis imaging. Accordingly, it is also important to develop a data processing technique for properly classifying the areas on a sample and visualizing the classification from only the result of mass-analysis imaging, without relying on the information obtained from the optical microscope image.

BACKGROUND ART DOCUMENT

Patent Document

Patent Document 1: US-A1 2009/0289184

Non-Patent Document

Non-Patent Document 1: Kiyoshi Ogawa et al., "Kenbi Shitsuryou Bunseki Souchi No Kaihatsu," ("Research and Development of Mass Microscope") *Shimadzu Review*, Shimadzu Corporation, Mar. 31, 2006, vol. 62, nos. 3•4, pp. 125-135

Non-Patent Document 2: Takahiro Harada et al., "Kenbi Shitsuryou Bunseki Souchi Ni Yoru Seitai Soshiki Bunseki," ("Biological Tissue Analysis Using Mass Microscope") *Shimadzu Review*, Shimadzu Corporation, Apr. 24, 2008, vol. 64, nos. 3•4, pp. 139-146

SUMMARY OF THE INVENTION

Problem to Be Solved by the Invention

The present invention has been developed to solve the aforementioned problems, and the objective thereof is to provide a mass-analysis data processing method and system capable of processing a large amount of data collected by an imaging mass analysis to present, in an intuitively understandable form for analysis operators, significant information for discriminating different kinds of tissue on a sample or detecting a specific portion on the sample.

Means for Solving the Problems

A mass-analysis data processing method according to a first aspect of the present invention aimed at solving the aforementioned problem is a method for processing mass-analysis data collected by a mass spectrometer capable of performing a mass analysis on each of a plurality of micro areas within a two-dimensional area on a sample and acquiring an optical microscope image on the sample, including:

a) a small-area specifying step, in which, based on a visual judgment on an optical microscope image taken for a predetermined area on the sample, a small area that can be regarded as having the same composition or exhibiting the same property is specified for each of two or more portions having different compositions or exhibiting different properties;

b) an expression information extracting step, in which, for each small area specified in the small-area specifying step as an area having the same composition or exhibiting the same property, the mass-analysis data obtained for all the micro areas included in the small area are processed to extract, as expression information of the concerned small area, peak information that is highly common among the micro areas; and c) a specific expression information extracting step, in which the small areas having different compositions or exhibiting different properties are compared in terms of their expression information to extract, for each small area, specific expression information from all the expression information of the concerned small area.

A second aspect of the present invention aimed at solving the previously described problem is a system for carrying out the method for processing mass-analysis data according to the first aspect of the present invention. That is to say, it is a mass-analysis data processing system for processing mass-analysis data collected by a mass spectrometer capable of performing a mass analysis on each of a plurality of micro areas within a two-dimensional area on a sample and acquiring an optical microscope image on the sample, including:

a) a small-area specifying section for specifying, based on a visual judgment on an optical microscope image taken for a predetermined area on the sample, a small area that can be regarded as having the same composition or exhibiting the same property, for each of two or more portions having different compositions or exhibiting different properties;

b) an expression information extracting section for processing, for each small area specified by the small-area specifying section as an area having the same composition or exhibiting the same property, the mass-analysis data obtained for all the micro areas included in the small area, to extract, as expression information of the concerned small area, peak information that is highly common among the micro areas; and c) a specific expression information extracting section for comparing the small areas having different compositions or exhibiting different properties in terms of their expression information to extract, for each small area, specific expression information from all the expression information of the concerned small area.

When the sample is a biological sample, such as a section of a living organism, the "portion having the same composition or exhibiting the same property" is, for example, the same kind of biological tissue, and the "portion having a different composition or exhibiting a different property" is, for example, a different kind of biological tissue. It should be noted that the same kind of biological tissue may have its composition or property changed due to cancer or similar lesion. In such a case, the normal and lesion sites within the same kind of biological tissue can be regarded as the "portions having different compositions or exhibiting different properties."

In the mass-analysis data processing method according to the first aspect of the present invention, the small-area specifying step may include the sub-steps of displaying, on a screen of a display device, an optical microscope image corresponding to a predetermined area on the sample and allowing an analysis operator to visually judge the displayed image, to locate a small area that can be regarded as a portion having the same composition or exhibiting the same property or as a portion having a different composition or exhibiting a different property based on the color, pattern and/or other kinds of information, and to specify the range of the small area in a predetermined manner, e.g. by using a pointing device. In this case, the analysis operator specifies each small area based on his or her own visual judgment.

Alternatively, in the mass-analysis data processing method according to the first aspect of the present invention, the small-area specifying step may include the sub-step of performing an image recognition process on an optical microscope image to distinguish different portions having different colors, patterns or other visual properties or a portion where a boundary is present, and automatically specify, based on the result of the distinguishing process, a small area that can be regarded as a portion having the same composition or exhibiting the same property or as a portion having a different composition or exhibiting a different property. In this case, the analysis operator does not need to make personal judgments since each small area is automatically specified on the basis of a visual judgment by a computer or the like.

In the mass-analysis data processing method according to the first aspect of the present invention, for example, when the sample is a biological sample, the expression information extracting step is performed in such a manner that, for each small area specified in the small-area specifying step as an area that can be regarded as the same kind of biological tissue, the mass-analysis data obtained for all the micro areas included in that small area are processed to extract, as expression information characteristic of that small area, peak information that is highly common in the small area. Normally, many pairs of mass-to-charge ratios and intensities exist as expression information for each small area.

One example of the highly common peak information is the combination of the mass-to-charge ratio and intensity value of a peak that is frequently detected in the same kind of biological tissue and at the same mass-to-charge ratio (or more exactly, within a range of mass-to-charge ratios that can be regarded as the same when the mass-resolving power or other factors are taken into account).

In the expression information extracting step, only the information obtained for one kind of biological tissue is concerned. Therefore, it is uncertain whether the expression information obtained for a small area can be used as characteristic information for distinguishing the biological tissue in the concerned small area from other kinds of biological tissue. Accordingly, in the subsequent, specific expression information extracting step, different small areas having different compositions of the biological tissue are compared in terms of their expression information, and even if there is any information which characterizes a small area, the information will be excluded if it is highly common among different kinds of biological tissue and therefore inappropriate for distinguishing them. As a result, for each small area, only the expression information that is truly specific to that small area is extracted.

The specific expression information to be eventually extracted for each small area is obtained under the classifications of the areas based on an optical microscope image on the sample. Therefore, this information can be considered to be a combination of information obtained by the optical microscopic observation and information obtained by mass analysis. Accordingly, for example, if different kinds of biological tissue are distinguishable on an optical microscope image, or if normal and lesion sites of the same kind of biological tissue are distinguishable, it is possible to obtain expression information that accurately characterizes each of those portions or sites.

A mass-analysis data processing method according to a third aspect of the present invention aimed at solving the previously described problem is a method for processing mass-analysis data collected by a mass spectrometer for performing a mass analysis on each of a plurality of micro areas within a two-dimensional area on a sample, including:

a) a process-target setting step, in which one micro area within the two-dimensional area on the sample and another micro area that spatially neighbors the aforementioned one micro area are selected; and b) a common expression information extracting step, in which the mass-analysis data obtained for the two micro areas selected in the process-target setting step are processed to extract, as expression information, peak information that is highly common to the two micro areas.

A fourth aspect of the present invention aimed at solving the previously described problem is a mass-analysis data processing system for carrying out the mass-analysis data processing method according to the third aspect of the present invention. That is to say, it is a system for processing mass-analysis data collected by a mass spectrometer for performing a mass analysis on each of a plurality of micro areas within a two-dimensional area on a sample, including:

a) a process-target setting section for selecting one micro area within the two-dimensional area on the sample and another micro area that spatially neighbors the aforementioned one micro area; and b) a common expression information extracting section for processing the mass-analysis data obtained for the two micro areas selected by the process-target setting section, to extract, as expression information, peak information that is highly common to the two micro areas.

In the mass-analysis data processing method or system according to the third or fourth aspect of the present invention, for a given pair of micro areas spatially neighboring each other, an attempt is made to extract common expression information from the mass-analysis data obtained for the two micro areas. A successful extraction of common expression information means that the two micro areas are most likely to belong to a portion having the same composition or exhibiting the same property. Conversely, if no common expression information can be extracted, it is likely that the two micro areas respectively belong to different portions having different compositions or exhibiting different properties.

In the first mode of the mass-analysis data processing method according to the third aspect of the present invention, a system capable of performing a mass analysis on each of a plurality of micro areas on a sample and acquiring an optical microscope image on the sample is used as the mass spectrometer, wherein:

the process-target setting step includes a small-area specifying step in which, based on a visual judgment on an optical microscope image taken for a predetermined area on the sample, a small area that can be regarded as having the same composition or exhibiting the same property is specified, and all combinations of two spatially neighboring micro areas are selected for each and every micro area included in the specified small area; and in the common expression information extracting step, common expression information is extracted for each of the combinations of the micro areas selected in the process-target selecting step.

In this mode of the method, similar to the first aspect of the present invention, an optical microscope image corresponding to a predetermined area on a sample may be displayed on a screen of a display device to allow an analysis operator to visually judge the displayed image, to locate a sample range that can be regarded as a portion having the same composition or exhibiting the same property or as a portion having a different composition or exhibiting a different property based on the color, pattern and/or other kinds of information, and to specify a small area of an appropriate size within that sample range in a predetermined manner, e.g. by using a pointing device. In this case, the common expression information to be extracted in the common expression information extracting step is obtained under the classifications of the areas based on an optical microscope image on the sample. Therefore, the information can be considered to be a combination of information obtained by the optical microscopic observation and information obtained by mass analysis. Accordingly, for example, if different kinds of biological tissue are distinguishable on an optical microscope image, or if normal and lesion sites of the same kind of biological tissue are distinguishable, it is possible to obtain common expression information that accurately characterizes each of those portions or sites.

In the mass-analysis data processing method according to the second mode of the third aspect of the present invention, a specific-area determining process for determining an area composed of a set of micro areas for which common expression information can be extracted is performed by repeating the following process until the common expression information can no longer be extracted:

when common expression information for a given pair of micro areas selected in the process-target setting step has been successfully extracted in the common expression information extracting step, the process-target setting step is iteratively performed to select each and every possible pair of micro areas, with one micro area selected from the given pair of micro areas and the other micro area selected from a group of micro areas neighboring the selected one of the pair of micro areas, and the common expression information extracting step is performed to extract common expression information by using the mass-analysis data obtained for the selected pair of micro areas.

In this second-mode method, an optical microscope image of an area on a sample is not always necessary; based on the mass-analysis data, a group of spatially neighboring micro areas having common expression information will be automatically and sequentially searched for. As a result, for example, a certain kind of biological tissue or a lesion site within a certain kind of biological tissue will be distinguishable as one area. Since the searching process requires no information of optical microscope images, it is possible to locate a boundary between different kinds of biological tissue even when no clear boundary is discernible between the aforementioned different kinds of biological tissue on an optical microscope image.

Effect of the Invention

With the mass-analysis data processing methods according to the first and third aspects of the present invention as well as the mass-analysis data processing systems according to the second and fourth aspects of the present invention, it is possible to properly and accurately collect information that is specifically expressed on a specific portion of a sample, based on a large amount of data collected by an imaging mass analysis. For example, in the case of a human biological sample, it is possible to separately obtain information characterizing a lesion site (e.g. cancer) and information characterizing the other, normal sites. Such information is useful, for example, to determine the spread of the lesion site.

Particularly, in the cases of the mass-analysis data processing method according to the first mode of the first or third aspect of the present invention as well as the system for carrying out this method, since information obtained from an optical microscope image whose spatial resolution is much higher than that of a mass analysis result image is used to acquire common expression information, the accuracy of the common expression information can be significantly improved in some cases, e.g. when it is easy to visually distinguish between different kinds of biological tissue or between lesion and normal sites. Furthermore, with the mass-analysis data processing method according to the first mode of the first or third aspect of the present invention as well as the system for carrying out this method, it is possible to extract cell-specific expression information in a single cancer cell.

In the cases of the mass-analysis processing data method according to the second mode of the third aspect of the present invention as well as the system for carrying out this method, even if no difference in color, pattern or other morphological properties is discernible among different kinds of biological tissue on a sample, or even if the optical microscope image is obscured by a matrix applied for the sake of matrix-assisted laser desorption ionization, it is possible to determine the range of a specific kind of biological tissue or a lesion site. Even an unknown kind of spatial expression cluster that is invisible on the optical microscope image of the sample can be detected.

BRIEF DESCRIPTION OF THE DRAWINGS

FIG. 2 is a flowchart showing the steps of a process for extracting area-specific expression information by the imaging mass spectrometer of the present embodiment.

FIGS. 3A-3C are conceptual diagrams for explaining the area-specific expression information extracting process shown in FIG. 2.

FIG. 4 is a flowchart showing the steps of a process for extracting cell-specific expression information by the imaging mass spectrometer of the present embodiment.

FIG. 5 is a conceptual diagram for explaining the cell-specific expression information extracting process shown in FIG. 4.

FIG. 6 is a flowchart showing the steps of a process for extracting space-specific expression information by the imaging mass spectrometer of the present embodiment.

FIG. 9A is an average mass spectrum showing the mass-to-charge ratios of the substances newly found as a result of the space-specific expression information extracting process performed on the sample shown in FIG. 8, and FIG. 9B shows mapping images of the ions respectively detected at the aforementioned mass-to-charge ratios.

BEST MODE FOR CARRYING OUT THE INVENTION

Figure 1:
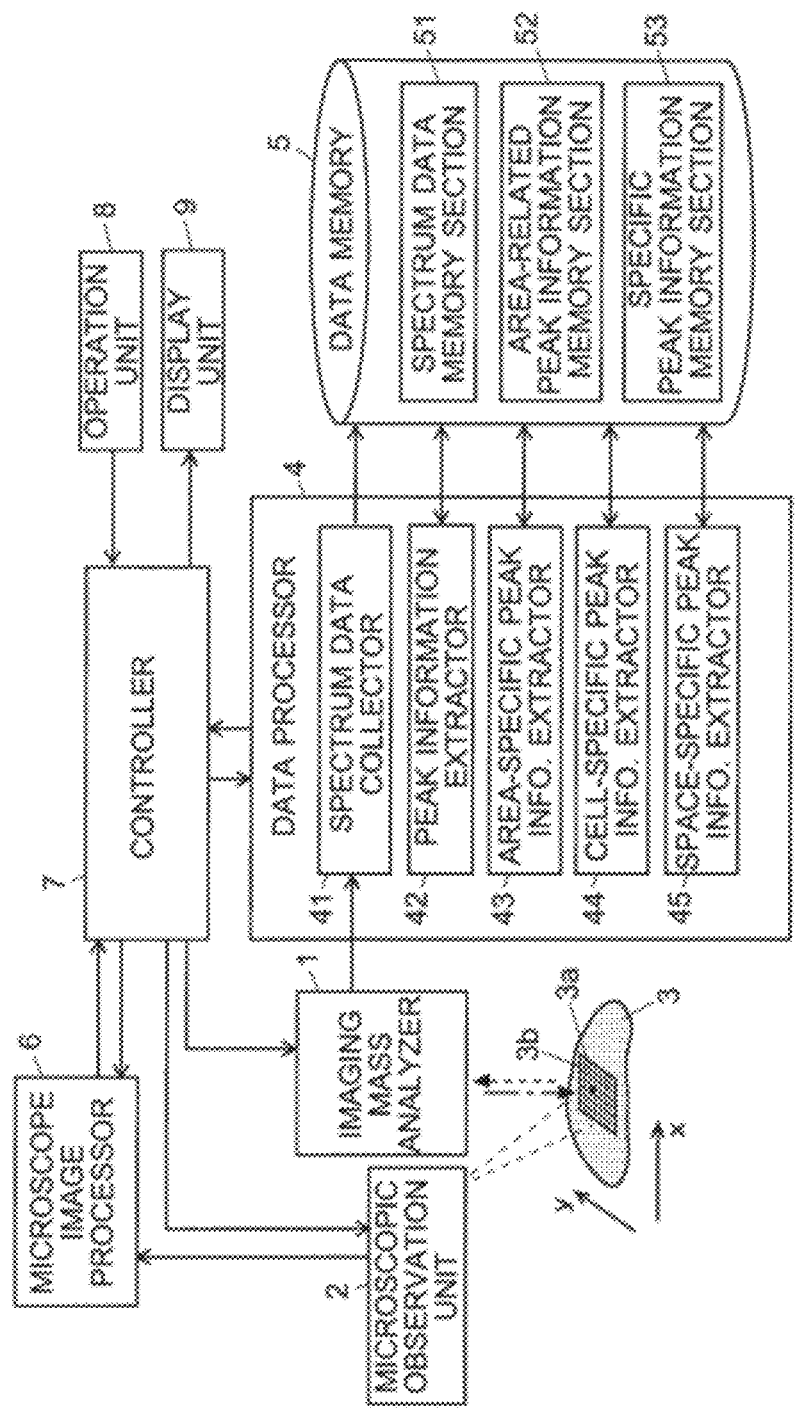
FIG. 1 is a schematic configuration diagram of one embodiment of an imaging mass spectrometer for carrying out the mass-analysis data processing method according to the present invention.

One embodiment of an imaging mass spectrometer for carrying out the mass-analysis data processing method according to the present invention is hereinafter described with reference to the attached drawings. FIG. 1 is a schematic configuration diagram of the imaging mass spectrometer according to the present embodiment.

This imaging mass spectrometer includes: an imaging mass analyzer 1 for performing a mass analysis on each measurement point (micro area) 3b within a two-dimensional target area selected as the target of measurement on a sample 3; a microscopic observation unit 2 for taking optical microscope images of a portion or the entire of the two-dimensional target area 3a on the sample 3; a data processor 4 for processing and analyzing mass spectrum data collected by the imaging mass analyzer 1; a data memory 5 for storing various kinds of data, including mass spectrum data; a microscope-image processor 6 for processing image signals obtained with the microscopic observation unit 2 to create an optical microscope image; a controller 7 for controlling these functional components; and an operation unit 8 as well as a display unit 9, both being connected to the controller 7.

Though not shown, the imaging mass analyzer 1 includes a matrix-assisted laser desorption ionizer (MALDI), an ion transport optical system, an ion trap, a time-of-flight mass analyzer, an ion detector and other elements, as described in Non-Patent Document 1 or 2, to perform a mass analysis over a specific range of mass-to-charge ratios for each micro area 3b having a predetermined size in each of the x and y directions. The imaging mass analyzer 1 further includes a stage driver for precisely moving a stage (not shown), with the sample 3 placed thereon, along the two axes of x and y. With this mechanism, mass spectrum data for a given area of any size can be collected by performing a mass analysis every time the sample 3 is moved stepwise by a predetermined width.

The data processor 4 includes, as its functional blocks, a spectrum data collector 41, a peak information extractor 42, an area-specific peak information extractor 43, a cell-specific peak information extractor 44, and a space-specific peak information extractor 45. The data memory 5 is virtually divided into a spectrum data memory section 51, an area-related peak information memory section 52, and a specific peak information memory section 53. At least a portion of the functions of the data processor 4, data memory 5, microscope-image processor 6, controller 7 and other components are realized by running a dedicated processing and controlling software program installed on a personal computer.

As one characteristic data-processing method carried out in the imaging mass spectrometer of the present embodiment, the process for extracting area-specific expression information is hereinafter described with reference to FIGS. 2 and 3. FIG. 2 is a flowchart showing the steps of the process for extracting area-specific expression information, and FIGS. 3A-3C are conceptual diagrams for explaining the process for extracting area-specific expression information.

As a premise for the data processing, the imaging mass analyzer 1 under the control of the controller 7 performs a mass analysis for each and every measurement point 3b within a predetermined two-dimensional target area 3a on a sample 3. Subsequently, the spectrum data collector 41 collects mass spectrum data of a predetermined range of mass-to-charge ratios for each measurement point 3b and stores the data in the spectrum data memory section 51.

When an analysis operator, through the operation unit 8, gives a command to initiate the data processing, the microscopic observation unit 2 under the control of the controller 7 takes an optical microscope image of a portion or the entirety of the two-dimensional target area 3a on the sample 3, and the microscope-image processor 6 reconstructs a two-dimensional image from the image signals and displays the image on the screen of the display unit 9. The analysis operator visually examines the displayed optical microscope image, determines a range of the same kind of biological tissue based on the color, pattern or other visual properties, and specifies a small area for each range of the same kind of biological tissue by using the operation unit (pointing device) 8 (Step S1). It is hereinafter assumed that, for an optical microscope image shown in FIG. 3A, three small areas A, B and C as shown in FIG. 3B have been specified. For example, the small areas A, B and C may be a cancerous part of a liver, a normal part of a liver, and an interstitial tissue, respectively.

After the small areas to be observed (or processed) have been fixed, the peak information extractor 42 selects one of the specified small areas, reads from the spectrum data memory section 51 mass spectrum data for all the measurement points 3b included in the selected small area, and extracts peak information from the read data (Step S2). More specifically, for a given piece of mass spectrum data, a window having a predetermined small width in the m/z direction (the X-axis direction of the mass spectrum) is set, and an m/z value corresponding to the largest intensity value (in the Y-axis direction of the mass spectrum), i.e. the largest amount of expression, within the window is located. The located m/z value and the corresponding intensity value are recorded as the molecular ion expression information (peak) within that window. While the window is moved stepwise in the m/z direction, the molecular ion expression information is obtained for each position of the window until the entire m/z range is completed. In this manner, a set of peak information for one mass spectrum data is extracted by scanning the mass spectrum in the m/z direction. The peak information is similarly extracted from the mass spectrum data of each measurement point 3b.

The peak information obtained in the previously described manner contains noise information due to various factors. To exclude such noise information to the greatest possible extent, a common peak method is applied to all the peak information obtained for the entire group of mass spectrums so as to extract highly reliable, crucial peak information (Step S3). For example, in the common peak method, any peak whose intensity is equal to or higher than a predetermined threshold at all the measurement points belonging to a specified range (or at a number of measurement points equal to or more than a predetermined proportion of the measurement points) is extracted as a common peak by computing the total of the amount of expression for each of the obtained m/z values by using a normal-distribution Gaussian kernel function and extracting any molecular ion expression information (peak) equal to or higher than the threshold from that distribution. After the peaks which probably originate from noises are removed in this manner, the peak information of each of the measurement points 3b is selected as crucial peak information for the concerned area and stored in the area-related peak information memory section 52. The positional coordinates of the measurement point 3b are also stored with the crucial peak information.

After that, whether or not any of the small areas specified in Step S1 remains to be processed is determined, and if any, the operation returns from Step S4 to S2 to repeat Steps S2 through S4. In this manner, expression information (peak information) for each kind of biological tissue is prepared in the area-related peak information memory section 52.

By using the operation unit 8, the analysis operator selects a plurality of kinds (normally, two kinds) of biological tissue (small areas) to be compared (Step S5). For example, the analysis operator can specify two small areas to be compared by indicating any one point within each of the two areas on an optical microscope image displayed on the screen of the display unit 9. After the small areas are selected, the area-specific peak information extractor 43 reads a set of peaks of expression information for each small area from the area-related peak information memory section 52 (Step S6).

The area-specific peak information extractor 43 compares different small areas in terms of their expression information to extract one or more area-specific peaks that can be used for distinguishing between those small areas (Step S7). Normally, one small area may have two or more area-specific peaks. To search for an area-specific peak set by combining a plurality of peaks, a machine learning algorithm, such as the AdaBoost algorithm used in the machine learning theory, can be used to extract an area-specific peak set by statistical processing. The searching method using this algorithm successfully works even in the special case where there is only one area-specific peak. After the extracted area-specific peak set is stored in the specific peak information memory section 53 (Step S8), the entire process is completed. It should be noted that a variety of commonly known statistical determination techniques other than the AdaBoost algorithm can naturally be used for searching for the area-specific peak set.

The crucial peak information deduced for each area in Step S3 has originally been obtained for each small area selected by a visual judgment of an analysis operator on an optical microscope image. Therefore, when the portion for which expression information needs to be collected by using mass-analysis data (such as a normal or cancerous site of the liver) is to some extent clearly recognizable on the optical microscope image, it is possible to collect area-specific expression information with high accuracy by utilizing visual judgment.

As another characteristic data-processing method carried out in the imaging mass spectrometer of the present embodiment, the process for extracting cell-specific expression information is hereinafter described with reference to FIGS. 4 and 5. FIG. 4 is a flowchart showing the steps of the process for extracting cell-specific expression information, and FIG. 5 is a conceptual diagram for explaining the process for extracting cell-specific expression information.

When an analysis operator, through the operation unit 8, gives a command to initiate the data processing, the microscopic observation unit 2 under the control of the controller 7 takes an optical microscope image of a portion or the entirety of a two-dimensional target area 3a on the sample 3, and the microscope-image processor 6 reconstructs a two-dimensional image from the image signals and displays the image on the screen of the display unit 9. The analysis operator visually examines the displayed optical microscope image, determines a range of the same kind of biological tissue based on the color, pattern or other visual properties, and specifies an arbitrary range or specific point within the same kind of biological tissue by the operation unit (pointing device) 8 (Step S11). It is hereinafter assumed that, as shown in FIG. 5, a range A1 within a small area A that can be regarded as the same kind of biological tissue has been specified.

Next, the peak information extractor 42 arbitrarily selects two measurement points neighboring each other among all the measurement points included in the specified range (Step S12). Then, it reads mass spectrum data for the two measurement points from the spectrum data memory section 51, extracts peak information for each measurement point in the same manner as Step S2, and extracts common, crucial peak information in the same manner as Step S3 (Step S13). If no expression of common peaks has been recognized, the fact is temporarily recorded.

Subsequently, in Step S14, whether or not any other combination of two neighboring measurement points remains among all the measurement points within the initially specified range (e.g. A1) is determined, and if any, the operation returns to Step S12 to similarly perform the previously described process of Steps S12 through S14. As a result of repeating Steps S12 through S14, common crucial peak information is extracted for each and every combination of two neighboring measurement points among all the measurement points within the initially specified range.

Then, the cell-specific peak information extractor 44 collects common peak information of all pairs of the neighboring measurement points within the specified range. If the collected peak information is the same, i.e. if the same peak expression has been recognized at all the measurement points within the specified range, the fact can be interpreted as meaning that all of those measurement points are located on the same cell, or that the same kind of cell is present at any of those measurement points. Accordingly, the cell-specific peak information extractor 44 extracts the common peak information as highly reliable, cell-specific expression information and stores it in the specific peak information memory section 53 (Steps S15 and S16). If no common peak expression can be recognized among the measurement points within the specified range, it is possible to interpret the fact as meaning that the specified range encompasses two or more different kinds of cells. Accordingly, no cell-specific expression information will be stored in the specific peak information memory section 53.

In this manner, a piece of expression information, i.e. the m/z value and intensity value, specific to one cell can be obtained. Therefore, for example, it is possible to obtain useful information on a cancerous cell by extracting expression information specific to the cancerous cell.

In the previously described cell-specific expression information extracting process, an analysis operator needs to initially specify a range to be processed, referring to an optical microscope image. Alternatively, a range where common peak expression is recognizable can be determined by automatically and sequentially searching for measurement points at which common peak information can be found, without limiting the range to be processed. This is the space-specific expression information extracting process, which is one of the characteristic data-processing methods carried out in the imaging mass spectrometer of the present embodiment.

The process steps of this method are hereinafter described with reference to FIGS. 6 and 7. FIG. 6 is a flowchart showing the steps of the space-specific expression information process, and FIG. 7 is a conceptual diagram for explaining the space-specific expression information extracting process.

The space-specific peak information extractor 45 initially sets the coordinates of an arbitrary measurement point (Step S21). This measurement point may be selected automatically according to a predetermined algorithm or manually based on an instruction from an analysis operator through the operation unit 8. Next, the peak information extractor 42 selects another measurement point that spatially neighbors the initially set measurement point (Step S22). Then, it reads mass spectrum data for the two measurement points from the spectrum data memory section 51, extracts peak information for each measurement point in the same manner as Step S2, and extracts common, crucial peak information in the same manner as Step S3 (Step S23). If no common peak information can be found, the operation proceeds from Step S24 to Step S25, where the coordinates of the initially-set measurement point are changed, and returns to Step S22.

As already explained, if common peak information has been found for two measurement points whose coordinate positions neighbor each other on the two-dimensional surface, the fact can be interpreted as meaning that both measurement points are located on the same cell, or that the same kind of cell is present at both measurement points. Accordingly, the space-specific peak information extractor 45 expands the region of interest so that the measurement point selected in Step S22 as well as the measurement point initially set in Step S21 or S25 will be included in this region (Step S26). Then, for each measurement point included in the added portion of the region of interest, the space-specific peak information extractor 45 determines whether or not Steps S23 and S24 have already been performed for all pairs of the measurement points in question and the neighboring measurement points outside the expanded region of interest (Step S27). If any pair of measurement points remains to be processed, there is a possibility that the region of interest can be further expanded. Accordingly, that pair of measurement points remaining to be processed, with one measurement point located outside the region of interest, is selected as a new pair (Step S28), and the operation returns to Step S23.

Figure 7A:
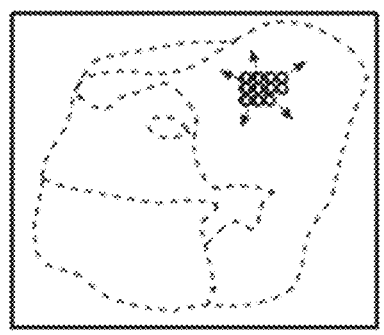
FIGS. 7A and 7B are conceptual diagrams for explaining the space-specific expression information extracting process shown in FIG. 6.

Thus, by repeating Steps S23, S24 and S26 through S28, each pair of measurement points neighboring each other on a two-dimensional area on which the imaging mass analysis has been performed is automatically and sequentially checked for the presence of common peak information (expression information), and if common peak information can be extracted, the pair is regarded as belonging to the same group, and the region of interest occupied by this group is expanded. FIG. 7A schematically shows this process. In this case, it does not matter whether or not different kinds of biological tissue can be distinguished on an optical microscope image. (Therefore, the boundaries of different kinds of biological tissue are indicated by dotted lines in FIG. 7A.)

Figure 7B:
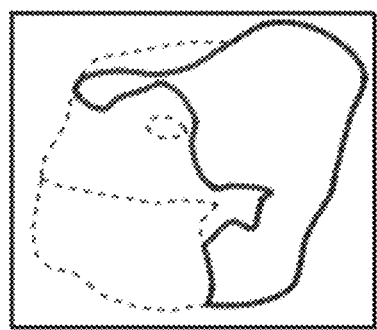

The region of interest continues to be expanded as long as common peak information can be found at the neighboring measurement points. When common peak information can no longer be found for any pair of the measurement point located immediately inside the boundary of the region of interest (i.e. within the region of interest) and the measurement point neighboring the aforementioned measurement point across the boundary (i.e. outside the region of interest), the operation proceeds from Step S27 to Step S29 to discontinue the expansion of the region of interest and fix the region. Then, an image showing the fixed region is displayed through the controller 7 on the screen of the display unit 9. For example, this image may show the region of the same kind of biological tissue as shown in FIG. 7B.

The process shown in FIG. 6 extracts only one region of interest. To extract two or more regions having common expression information, the process can be modified as follows: After one region of interest has been fixed in Step S29, the operation returns to Step S21, where, this time, a measurement point outside the already fixed region(s) of interest is set as a new initial measurement point, and starting from this point, the surrounding areas are automatically and sequentially searched for a region having common expression information. By repeating this process, the two-dimensional area on the sample 3 on which an imaging mass analysis has been performed can be divided into regions each of which has a similar morphological or biological property. This classification is based purely on the result of a mass analysis, and accordingly, can be based on a certain kind of information invisible on optical microscope images. For example, it is possible to determine a region occupied by a cancerous site that is visually indistinguishable from normal sites.

Figure 8:
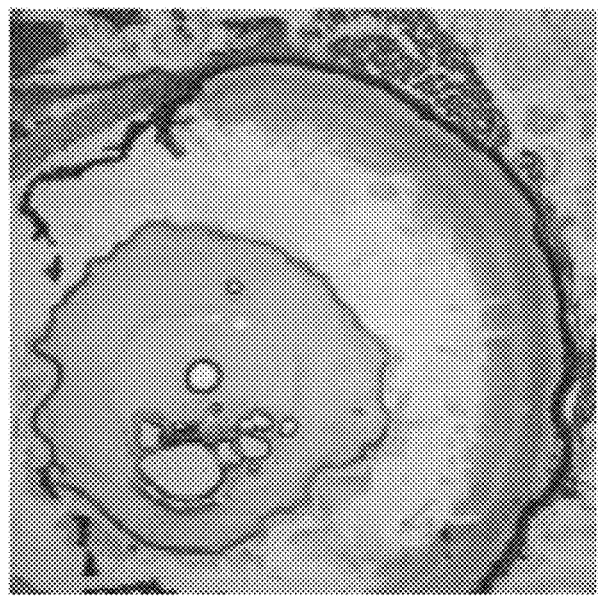
FIG. 8 is an optical microscope image of a measurement target on which a space-specific expression information extracting process was performed.

An example of the measurement using the previously described space-specific expression information extracting process is hereinafter described. FIG. 8 is an optical microscope image of a section of mouse retina used as the measurement target. Mass-analysis imaging of a section of mouse retina is a technique frequently used for system calibration or other purposes. The kinds of substances that can be detected from this sample are known from generally accessible documents (e.g. Hayasaka et al., "Development of imaging mass spectrometry (IMS) dataset extractor software", *IMS convolution Analytical and Bioanalytical Chemistry*, pp. 183-193, 2011).

The previously described space-specific expression information extracting process was performed on a set of mass-analysis imaging data (laser spot diameter of 10 µm; 250× 250 pixels) obtained from the sample shown in FIG. 8. As a result, 18 substances which had not been conventionally known had been extracted. FIG. 9A is an average mass spectrum showing the mass-to-charge-ratios of the 18 substances newly extracted by the present method. FIG. 9B show mapping images of the ions respectively detected at the aforementioned mass-to-charge ratios. These figures demonstrate that the space-specific expression information extracting process makes it possible to study the distribution of substances that cannot be clearly recognized on optical microscope images.

It should be noted that the previous embodiment is a mere example of the present invention, and any change, modification or addition appropriately made within the spirit of the present invention will naturally fall within the scope of claims of the present patent application.

EXPLANATION OF NUMERALS

1 . . . Imaging Mass Analyzer
2 . . . Microscopic Observation Unit
3 . . . Sample
3a . . . Two-Dimensional Target Area
3b . . . Measurement Point
4 . . . Data Processor
41 . . . Spectrum Data Collector
42 . . . Peak Information Extractor
43 . . . Area-Specific Peak Information Extractor
44 . . . Cell-Specific Peak Information Extractor
45 . . . Space-Specific Peak Information Extractor
5 . . . Data Memory
51 . . . Spectrum Data Memory Section
52 . . . Area-Related Peak Information Memory Section
53 . . . Specific Peak Information Memory Section
6 . . . Microscope-image Processor
7 . . . Controller
8 . . . Operation Unit
9 . . . Display Unit

The invention claimed is:

1. A mass-analysis data processing method for processing mass-analysis data collected by a mass spectrometer, comprising:

performing a mass analysis on each of a plurality of micro areas within a two-dimensional area on a sample and acquiring an optical microscope image on the sample;

a small-area specifying step, in which, based on a visual judgment on the optical microscope image taken for a predetermined area on the sample, a small area that can be regarded as having a same composition or exhibiting a same property is specified for each of two or more portions having different compositions or exhibiting different properties;

an expression information extracting step, in which, for each small area specified in the small-area specifying step as an area having the same composition or exhibiting the same property, the mass-analysis data obtained for all the micro areas included in the small area are processed to extract, as expression information of the small area, peak information that is highly common among the micro areas; and a specific expression information extracting step, in which the small areas having different compositions or exhibiting different properties are compared in terms of their expression information to extract, for each small area, specific expression information from all the expression information of the small area.

2. A mass-analysis data processing system for processing mass-analysis data, comprising:

a mass spectrometer for performing a mass analysis on each of a plurality of micro areas within a two-dimensional area on a sample and acquiring an optical microscope image on the sample;

a small-area specifying section for specifying, based on a visual judgment on the optical microscope image taken for a predetermined area on the sample, a small area that can be regarded as having a same composition or exhibiting a same property, for each of two or more portions having different compositions or exhibiting different properties;

an expression information extracting section for processing, for each small area specified by the small-area specifying section as an area having the same composition or exhibiting the same property, the mass-analysis data obtained for all the micro areas included in the small area, to extract, as expression information of the small area, peak information that is highly common among the micro areas; and a specific expression information extracting section for comparing the small areas having different compositions or exhibiting different properties in terms of their expression information to extract, for each small area, specific expression information from all the expression information of the small area.

3. A mass-analysis data processing method for processing mass-analysis data collected by a mass spectrometer, comprising:
performing a mass analysis on each of a plurality of micro areas within a two-dimensional area on a sample;
a process-target setting step, in which one micro area within the two-dimensional area on the sample and another micro area that spatially neighbors the aforementioned one micro area are selected; and
a common expression information extracting step, in which the mass-analysis data obtained for the two micro areas selected in the process-target setting step are processed to extract, as expression information, peak information that is highly common to the two micro areas.

4. The mass-analysis data processing method according to claim 3,
further comprising a step of acquiring an optical microscope image of a predetermined area on the sample; wherein:
the process-target setting step includes a small-area specifying step in which, based on a visual judgment on the optical microscope image, a small area that can be regarded as having a same composition or exhibiting a same property is specified, and all combinations of two spatially neighboring micro areas are selected for each and every micro area included in the specified small area; and
in the common expression information extracting step, common expression information is extracted for each of the combinations of the micro areas selected in the process-target selecting step.

5. The mass-analysis data processing method according to claim 3, wherein:
a specific-area determining process for determining an area composed of a set of micro areas for which common expression information can be extracted is performed by repeating a following process until the common expression information can no longer be extracted:
when common expression information for a given pair of micro areas selected in the process-target setting step has been successfully extracted in the common expression information extracting step, the process-target setting step is iteratively performed to select each and every possible pair of micro areas, with one micro area selected from the given pair of micro areas and the other micro area selected from a group of micro areas neighboring the given pair of micro areas, and the common expression information extracting step is performed to extract common expression information by using the mass-analysis data obtained for the selected pair of micro areas.

6. A mass-analysis data processing system for processing mass-analysis data, comprising:
a mass spectrometer for performing a mass analysis on each of a plurality of micro areas within a two-dimensional area on a sample;
a process-target setting section for selecting one micro area within the two-dimensional area on the sample and another micro area that spatially neighbors the aforementioned one micro area; and
a common expression information extracting section for processing the mass-analysis data obtained for the two micro areas selected by the process-target setting section, to extract, as expression information, peak information that is highly common to the two micro areas.

7. The mass-analysis data processing system according to claim 6, wherein:
the system further acquires an optical microscope image of a predetermine area on the sample;
the process-target setting section includes a small-area specifying section by which, based on a visual judgment on the optical microscope image, a small area that can be regarded as having a same composition or exhibiting a same property is specified, and all combinations of two spatially neighboring micro areas are selected for each and every micro area included in the specified small area; and
the common expression information extracting section extracts common expression information for each of the combinations of the micro areas selected by the process-target selecting section.

8. The mass-analysis data processing system according to claim 6, further comprising a specific-area determining section for determining an area composed of a set of micro areas for which common expression information can be extracted, by repeating a following process until the common expression information can no longer be extracted:
when common expression information for a given pair of micro areas selected by the process-target setting section has been successfully extracted by the common expression information extracting section, the process-target setting section iteratively selects each and every possible pair of micro areas, with one micro area selected from the given pair of micro areas and the other micro area selected from a group of micro areas neighboring the given pair of micro areas, and the common expression information extracting section extracts common expression information by using the mass-analysis data obtained for the selected pair of micro areas.

* * * * *